(12) United States Patent
Bennett

(10) Patent No.: US 7,314,459 B2
(45) Date of Patent: Jan. 1, 2008

(54) DIGIT-SUPPORTING THERAPEUTIC DEVICE FOR THE HAND

(76) Inventor: Marc Bennett, 695 Old Buffalo Grove Rd., Wheeling, IL (US) 60090

( * ) Notice: Subject to any disclaimer, the term of this patent is extended or adjusted under 35 U.S.C. 154(b) by 0 days.

(21) Appl. No.: 11/467,373

(22) Filed: Aug. 25, 2006

(65) Prior Publication Data

US 2006/0287626 A1    Dec. 21, 2006

Related U.S. Application Data

(63) Continuation-in-part of application No. 11/111,633, filed on Apr. 21, 2005.

(51) Int. Cl.
*A61F 5/00* (2006.01)
(52) U.S. Cl. .......................... 602/20; 602/22
(58) Field of Classification Search ............ 602/20–23; 128/877–879
See application file for complete search history.

(56) References Cited

U.S. PATENT DOCUMENTS

| | | | |
|---|---|---|---|
| 1,220,476 A * | 3/1917 | Ujdur | .......................... 602/22 |
| 1,594,151 A | 7/1926 | Chance | |
| 3,152,337 A | 10/1964 | Barry | |
| 3,189,025 A | 6/1965 | Yaklin | |
| 3,421,761 A | 1/1969 | Grant | |
| 3,533,405 A | 10/1970 | Collins | |
| 3,612,521 A | 10/1971 | Wendeborn | |
| 3,707,730 A | 1/1973 | Slider | |
| 4,128,097 A | 12/1978 | Bilinsky et al. | |
| 4,618,328 A | 10/1986 | Chi | |
| D294,878 S | 3/1988 | Banks | |
| 4,751,747 A | 6/1988 | Banks et al. | |
| 4,781,178 A * | 11/1988 | Gordon | .......................... 602/22 |
| 4,953,568 A | 9/1990 | Theisler | |
| 4,961,568 A | 10/1990 | Clark et al. | |
| 4,964,824 A | 10/1990 | Spencer | |
| 5,033,120 A | 7/1991 | Myers | |
| 5,313,667 A | 5/1994 | Levine | |
| 5,413,553 A | 5/1995 | Downes | |
| 5,749,097 A | 5/1998 | Garrett-Roe | |
| 5,762,621 A | 6/1998 | Schultz | |
| 5,848,440 A | 12/1998 | Pajarola | |
| 6,013,044 A | 1/2000 | Estwanik | |
| 6,029,277 A | 2/2000 | Picchione, II | |
| 6,095,994 A | 8/2000 | Spits | |
| 6,179,751 B1 | 1/2001 | Clears | |
| 6,887,212 B2 | 5/2005 | Bennett | |

* cited by examiner

*Primary Examiner*—Michael A. Brown

(57) ABSTRACT

A therapeutic hand device comprising a wrist-support section and a separate fingers-support section. The fingers-support section receives the index-finger and the middle finger, and is removably secured to the wrist-support section via a plurality of adjustable "VELCRO" straps. An open space is defined interiorly of, and delimited by, the fingers-support section and a portion of the wrist-support section whereby when the device is worn on a hand, an object may be inserted into the open space between the fingers-section and the thumb of the hand, with the adjustable straps being used to firmly hold the thumb and fingers in a pincer hold against an object, whereby the object may be held and manipulated with support and assistance by the device.

2 Claims, 11 Drawing Sheets

DIGIT-SUPPORTING THERAPEUTIC DEVICE FOR THE HAND

CROSS REFERENCE TO RELATED APPLICATION

The present application is a continuation-in-part of application Ser. No. 11/111,633, filed on Apr. 21, 2005.

BACKGROUND OF THE INVENTION

The present invention is directed a therapeutic device for the hand and for assisting a person in holding and gripping objects, as disclosed in Applicant's U.S. Pat. No. 6,887,212, which patent is incorporated by reference herein. The apparatus of the invention is a hand-worn device made to give total or partial support to the fingers of hand while using tools, and similar hand-carried and manipulatable items. The device of the invention supports the fingers of the hand in their functional positions, with the thumb able to oppose the fingers in either fixed or other desired positions.

Support devices for the hand are well-known. Examples of such are golf gloves, bowler's gloves, and the like. Some prior-art supports for the hand are therapeutic, by helping to support the hand, or one or more digits. Examples of prior-art therapeutic support devices for the hand are shown in the U.S. Pat. Nos. 3,152,337; 4,953,568; 5,762,621; 6,029,277; and 6,095,994. However, prior-art therapeutic hand-devices are either directed to treating a specific problem, or are cumbersome and bulky in use, preventing the digits from easily holding and manipulating a tool or object while at the same time providing the therapeutic support and treatment required.

SUMMARY OF THE INVENTION

It is, therefore, the primary objective of the present invention to provide a therapeutic device for the digits of a hand that allows the fingers of the hand to hold, use and manipulate an object, tool, and the like, while at the same time providing therapeutic support thereto.

It is a primary objective of the present invention to provide such a therapeutic device for the digits of a hand which allows the fingers or hand to hold, use and manipulate an object, tool, and the like, while at the same time providing therapeutic support thereto, which device therapeutically supports at least the thumb, index finger and middle finger, such that the index and middle fingers are held in opposition to the thumb.

The therapeutic hand device of the invention provides support to the fingers while performing a variety of pinches, including; tripod pinch, key pinch, and pincer. It provides gradable support by, for example, placing the finger-support sleeves closer to the distal intercarpophalangeal (DIP) joint, distally closer to the intercarpophalangeal (IP) joint , or proximally closer to the metacarpophalangeal (MP) joint. Support straps are adjustable to fasten the device to give more or less support, or may use tightly-fitting stretchable material for straps.

The occupational therapy device of the present invention offers gradable or variably-adjustable support to the thumb and index and middle fingers of the hand as it is used during routine activities, such as for holding a pencil, screwdriver, and the like, and consists of a separate, adjustably-mounted fingers-support section consisting of a pair of interconnected finger-support sleeves for the index finger and middle finger. The separate, adjustably-mounted fingers-support section is adjustably mounted to a wrist-support sleeve section via "VELCRO" straps, or other adjustable straps or mounting elements. In a first embodiment, the wrist-sleeve support section has a thumb opening through which the thumb of the wearer protrudes. The separate, adjustably-mounted fingers-support section is mounted to the wrist-sleeve support section by an adjustable, removable band or strip, and also has two adjustable tightening "VELCRO" strips or bands. One adjustable tightening "VELCRO" strip or band extends from the outer surface of index-finger sleeve, and the other adjustable tightening "VELCRO" strip or band extends from the outer surface of other middle-finger sleeve. These "VELCRO" strips or bands are removably secured to a chosen surface portion of the wrist-sleeve support section. The wrist-sleeve support section itself is preferably provided with a large surface area of the mating portion of the "VELCRO" strips or bands, whereby the degree to which the fingers-support section is brought into close proximity of the thumb hole of the wrist-sleeve support section may be varied to suit the user. In a second embodiment, the wrist-sleeve support section is provided with its own thumb sleeve, such as that disclosed in Applicant's U.S. Pat. No. 6,887,212, which thumb-sleeve may be adjustable to allow for the reception therein of different sizes of thumb. In this second embodiment, the fingers-support section is identical to that of the first embodiment and is adjustably secured to the thumb-sleeve support section via the mating half of the pair of hook-and-pile "VELCRO" straps or bands of fingers-support section. The thumb-section is adjustable by an adjustable "VELCRO" strap that surrounds the thumb when inserted in the thumb-section.

The present invention provides an occupational-therapy device that is more effective, safer, and allows a multitude of different tools to be used hitherto not possible with any glove or hand support. This new hand support utilizes a simple, yet effective, method of configuring and supporting the fingers of the hand while using virtually any type of hand tool. Some examples of hand tools it assists the hand to use are: a pen, spoon, fork, or knife, cell phone, screwdriver, electric or safely razors, power tools, baby bottles, cups or glasses, hair brushes or combs, knitting or crotchet needles, kitchen tools, golf clubs and tennis rackets.

BRIEF DESCRIPTION OF THE INVENTION

The invention will be more understood with reference to the accompanying drawing, wherein:

FIG. 10 is a rear isometric view showing the fingers-section of FIG. 4 removably and adjustably connected to the wrist-sleeve support section of the second embodiment of FIG. 8, with the thumb and two fingers being brought into opposite relationship for tripod-pinching for holding an object, such as a pencil.

DETAILED DESCRIPTION OF THE INVENTION

Figure 1:
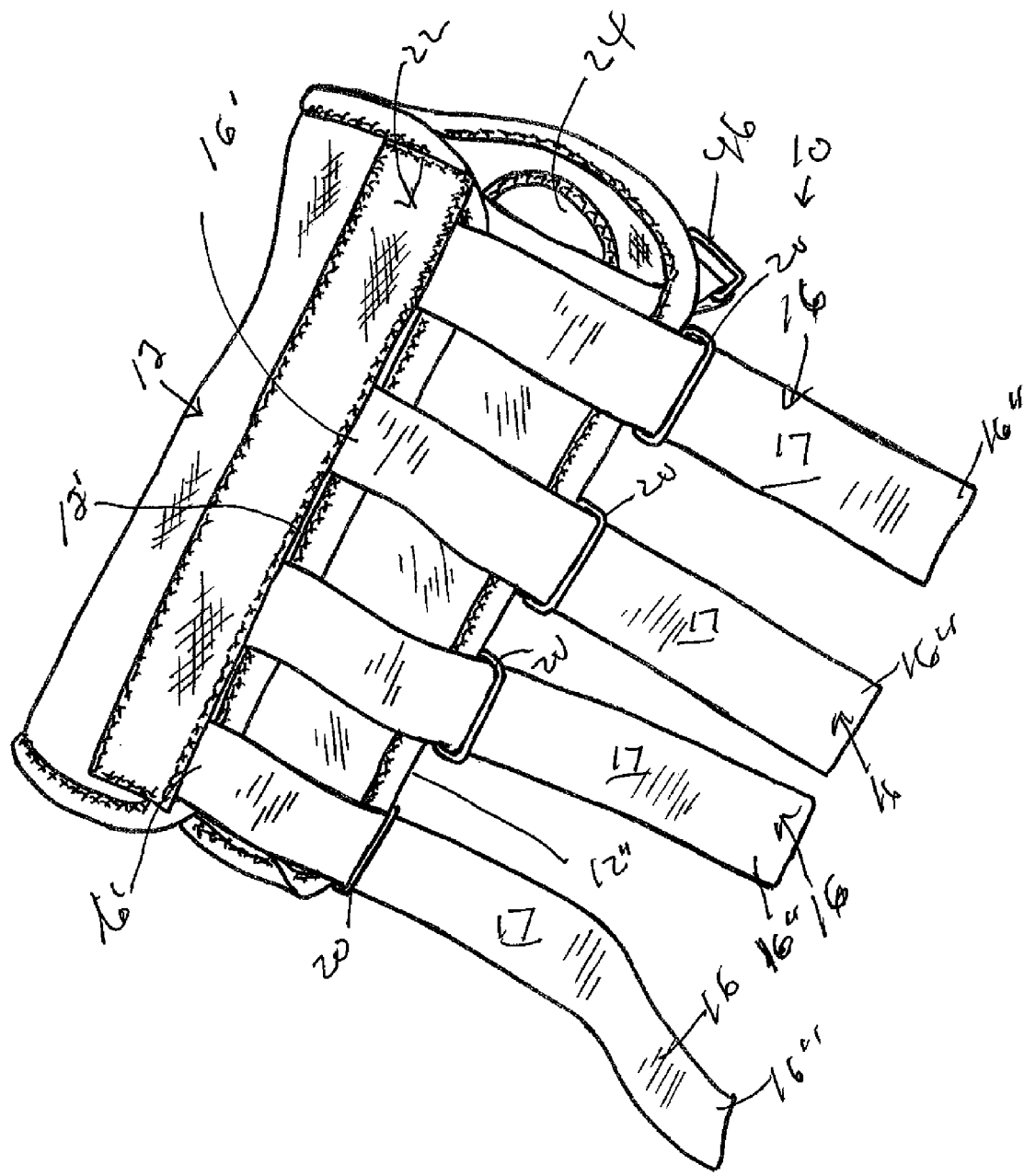
FIG. 1 is a front isometric view of the first embodiment of the separate wrist-sleeve support section of the digit-supporting therapeutic device for the fingers of a hand according to the invention.
Figure 2:
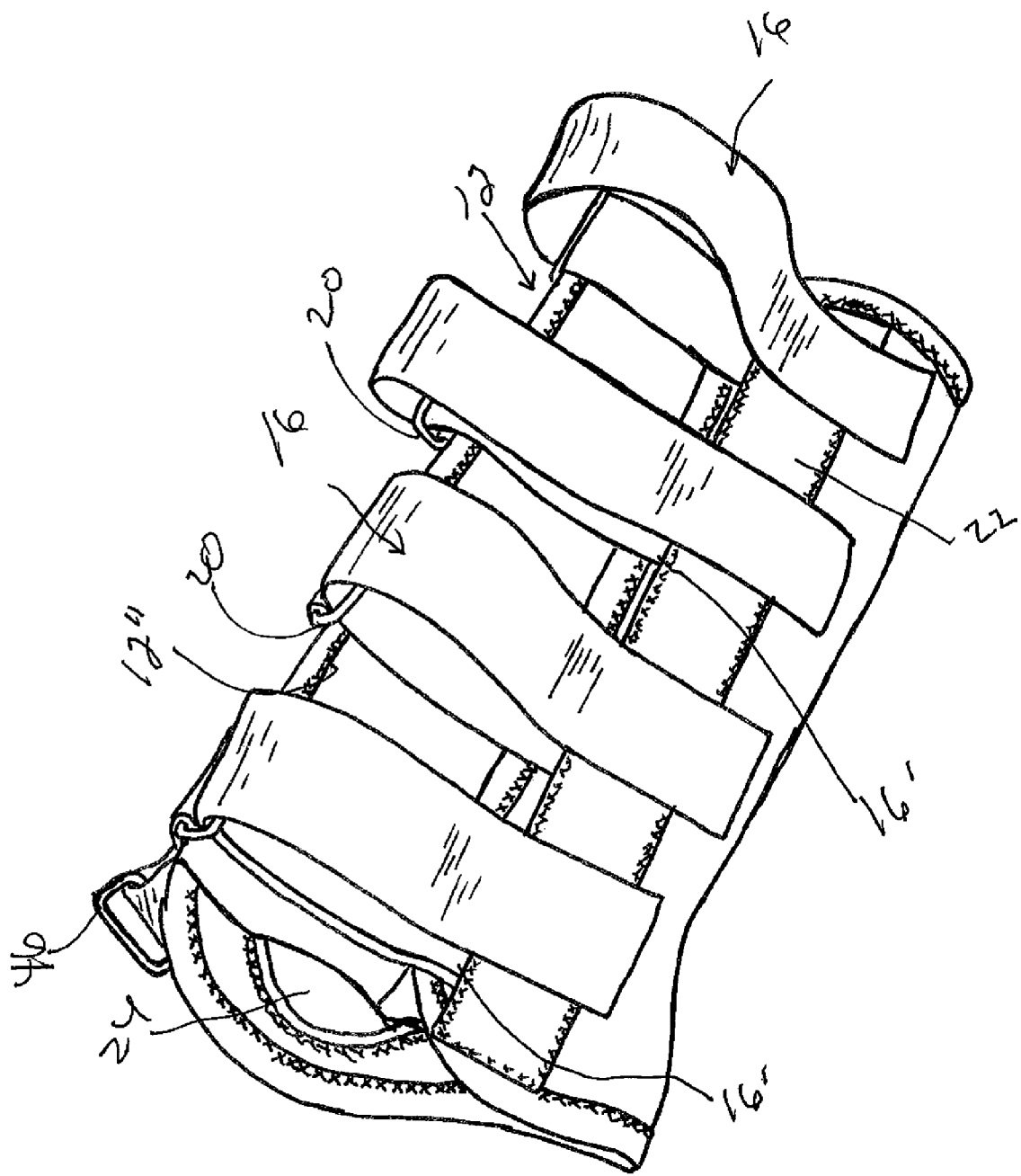
FIG. 2 is a rear isometric view of embodiment of FIG. 1.
Figure 3:
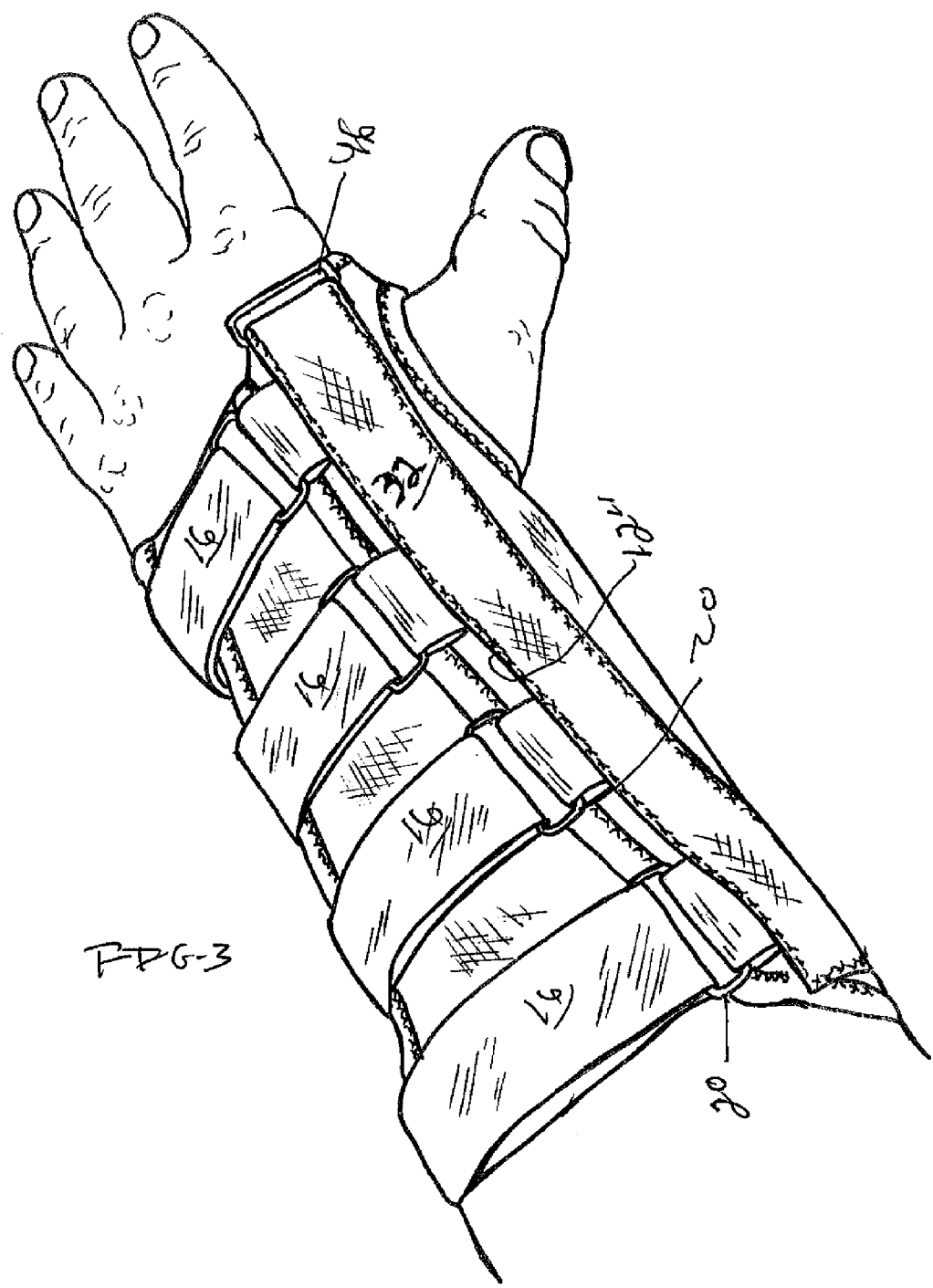
FIG. 3 is an isometric view of the separate wrist-sleeve support section of the digit-supporting therapeutic device for the fingers of a hand of FIG. 1 and shown worn on the hand of a user.
Figure 4:
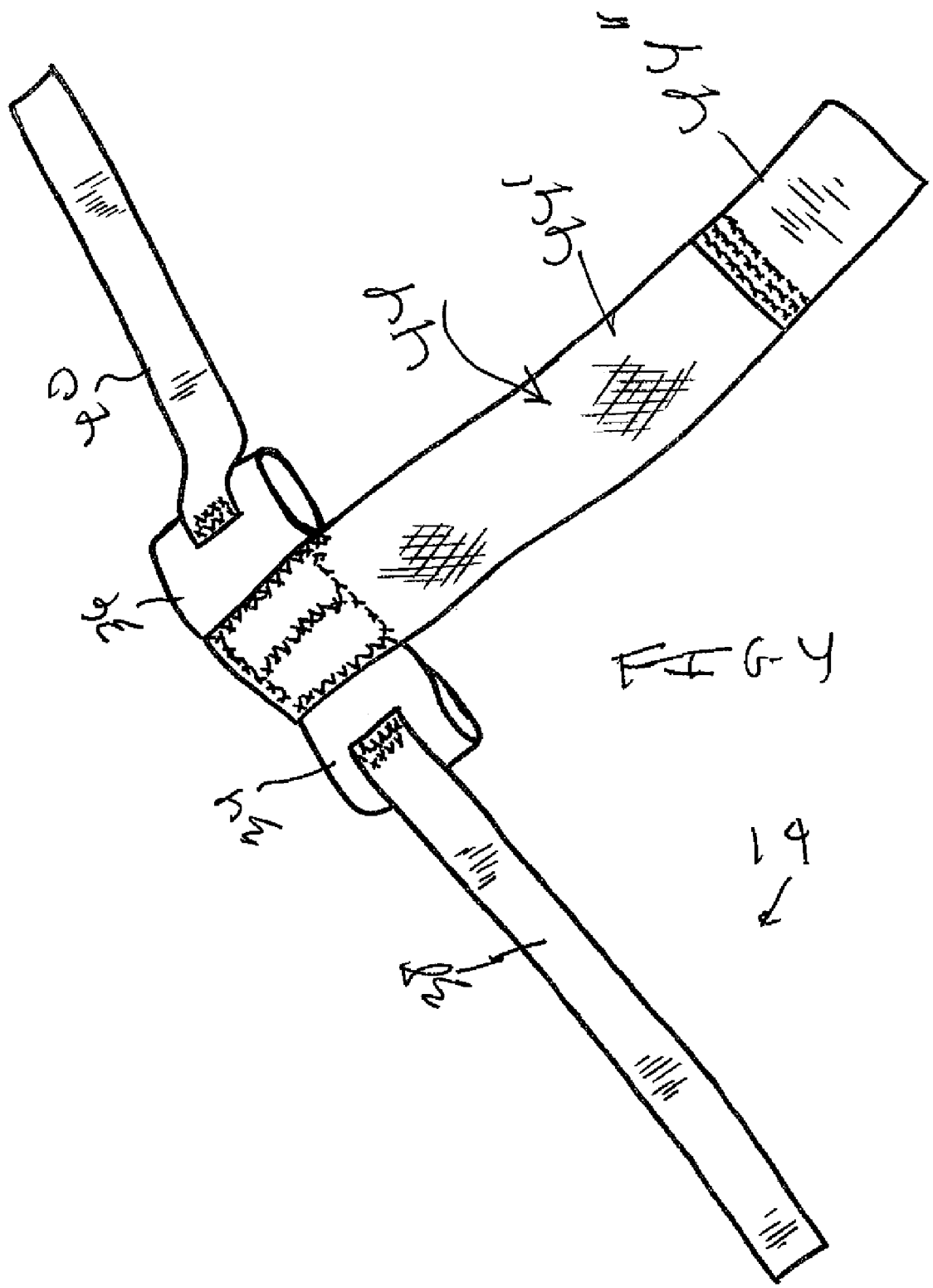
FIG. 4 is an isometric view of the separate fingers-support section of the digit-supporting therapeutic device for the fingers of a hand of FIG. 1.

Referring now to the drawings in greater detail, and in particular to FIGS. 1-7, there is shown the first embodiment of the digit-supporting therapeutic device for a hand of the invention. The device 10 consists a wrist-sleeve support section 12 (FIGS. 1-3) and a separate fingers-support section 14 (FIG. 4). The wrist-sleeve support section 12 is an elongated sleeve-like element to be worn on the wrist of a user in order to strengthen the wrist, as is well-known and conventional. The wrist-sleeve support section is provided with a plurality of adjustable fastening bands 16 each having a first end 16' secured to first end portion 12' of the wrist-sleeve support section. The second end portion 12" of the wrist-sleeve support section is provided with a like-number of loops 20 through which are inserted the other ends 16". The first end portion 12' of the wrist-sleeve support section is provided with a securing strip 22 that is the first half-section of a hook-and-pile fastener. Each of the adjustable fastening bands 16 is provided with the second, mating half-section of the hook-and-pile fastener on the interior surface 17 thereof, as seen in FIG. 1, whereby, after doubling back the strips 20, the interior surfaces 17 thereof mate with the strip 22 so that the wrist-sleeve support section 12 may be adjusted to fit variously-sized wrists. The wrist-sleeve support section is also provided with a thumb hole or opening 24 through which the thumb of the hand protrudes as seen in FIG. 3. The wrist-sleeve support section 12 is also provided with another "VELCRO" strip 32 at the second end portion 12" as best seen in FIG. 3 for purposes to described hereinbelow.

Referring now to FIG. 4, the fingers-support section 14 is shown and has a pair of finger-support sleeves 34, 36. The finger-support sleeve 34 is used to receive the index finger, while the finger-support sleeve 36 is used to receive the middle finger. The finger-support sleeves 34, 36 are preferably fixedly connected together along interior surfaces or edges to form one integral unit, although removable connection may also be used. Extending outwardly from each finger-support sleeve 34, 36 is an adjustable mounting strip or band 38, 40, respectively, with each having an end 34', 36' fixedly connected to the respective finger-support sleeve 34,36. Each band 38, 40 is the other mating half-section or portion of the hook-and-pile fastener band or strip 32 on the wrist-sleeve support section 12, whereby the fingers-support section 14 is brought toward and held opposite the thumb inserted through the thumb hole 24 of the wrist-sleeve support section. Thus, the "VELCRO" straps 34, 36 position, locate and maintain the finger-sleeves section 14 in the lateral direction for opposition to the thumb.

Figure 5:
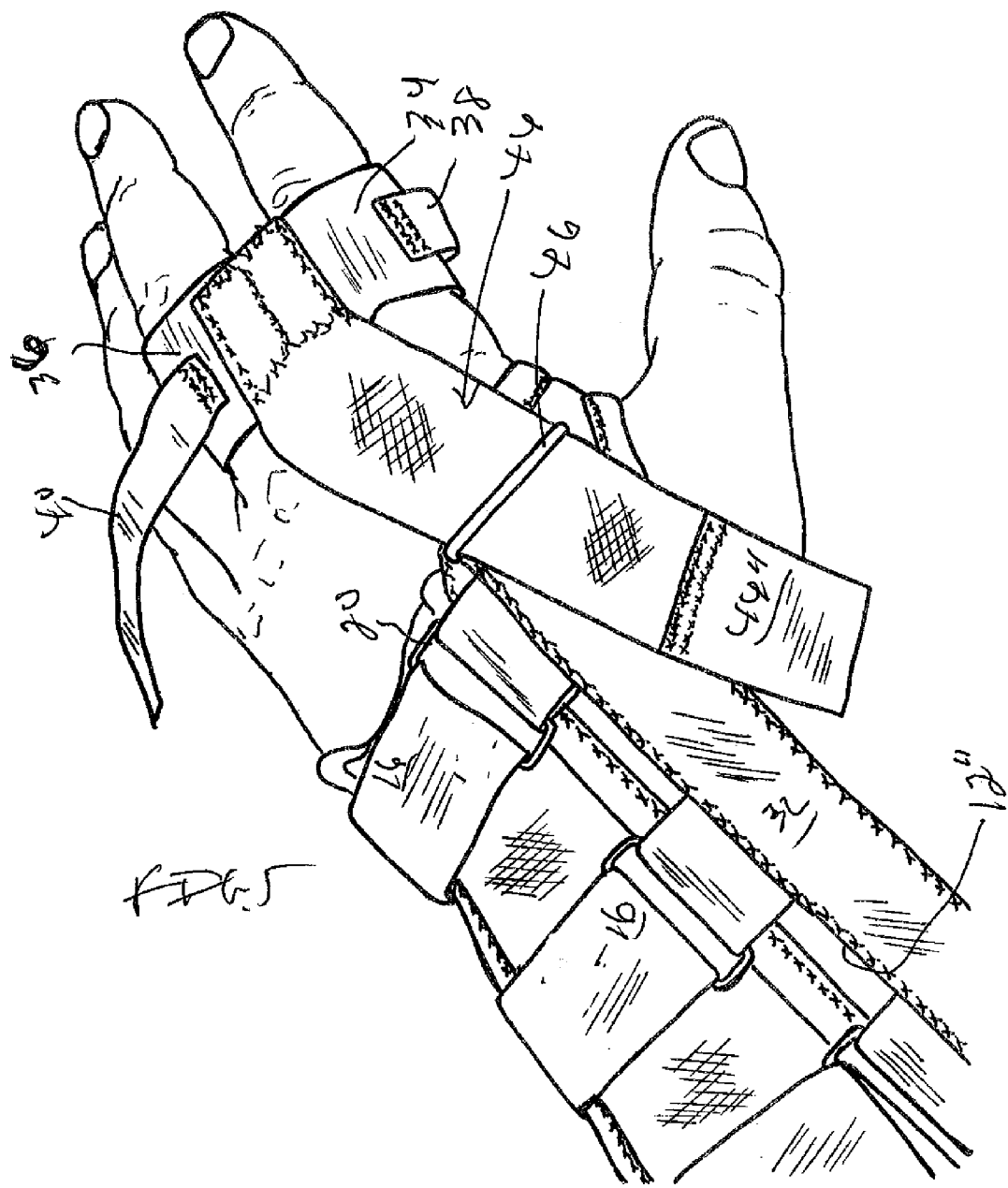
FIG. 5 is an isometric view similar to FIG. 3 but showing the removable mounting of the separate fingers-support section of FIG. 4 to the wrist-sleeve section of the digit-supporting therapeutic device for the fingers of a hand of FIG. 1.
Figure 6:
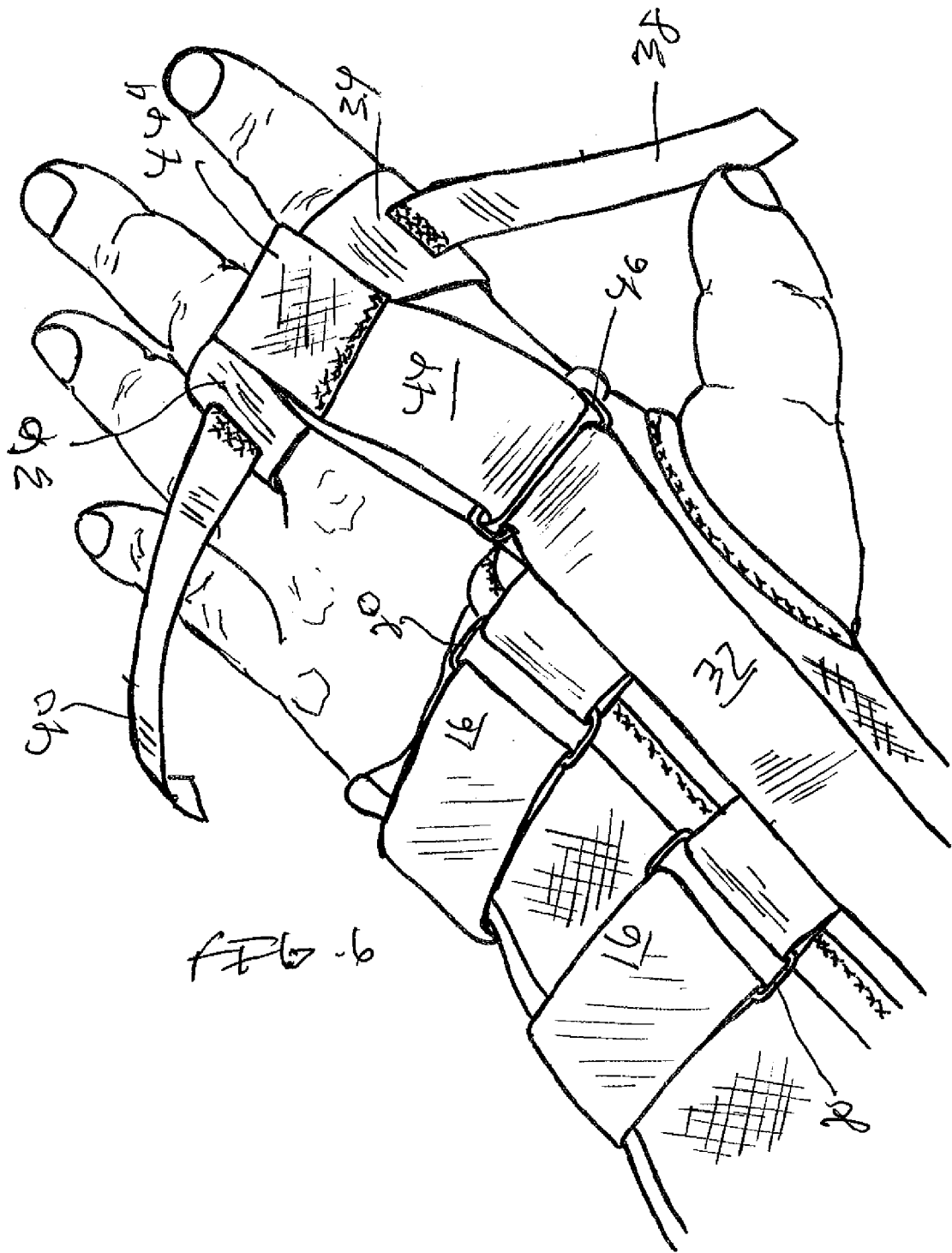
FIG. 6 is an isometric view similar to FIG. 5 showing the separate fingers-support section removably connected to the wrist-sleeve section of the digit-supporting therapeutic device for the fingers of a hand of FIG. 1.

The fingers-support section 14 is also provided with another, elongated central fastening strap or band 44 extending substantially from the mid-section thereof where the two finger-support sleeves 34, 36 are connected together. The strap 44 consists of a main portion 44' provided with the first half-section or portion of a hook-and-pile fastening element, and an end portion 44" consisting of the other, mating half of the hook-and-pile fastening element. The strap 44 cooperates with loop 46 of the wrist-sleeve support section, which loop 46 is located adjacent the edge of the strap 32, as best seen in FIG. 3. The strap 44 mounts the fingers-support section 14 to the wrist-sleeve support section by passing the end portion 44" through the loop and doubling back the end portion 44" and fastening its half of the hook-and-pile fastener to the mating half on the main portion 44 (FIGS. 5 and 6). The distance the fingers-support section is positioned from the wrist-sleeve support section, and, therefore, from the thumb hole 24 thereof, is thereby adjustable depending upon the size of the hand of the user. The strap 44 allows vertical adjustment of the fingers-support section relative to the thumb in order to accommodate variously-sized hands and also to allow the best orientation of the finger-support section relative to the thumb. The strap 44 extends substantially at an angle, such as a right angle, with respect to the extent of the other straps 38, 40 as seen in FIG. 4.

Figure 7:
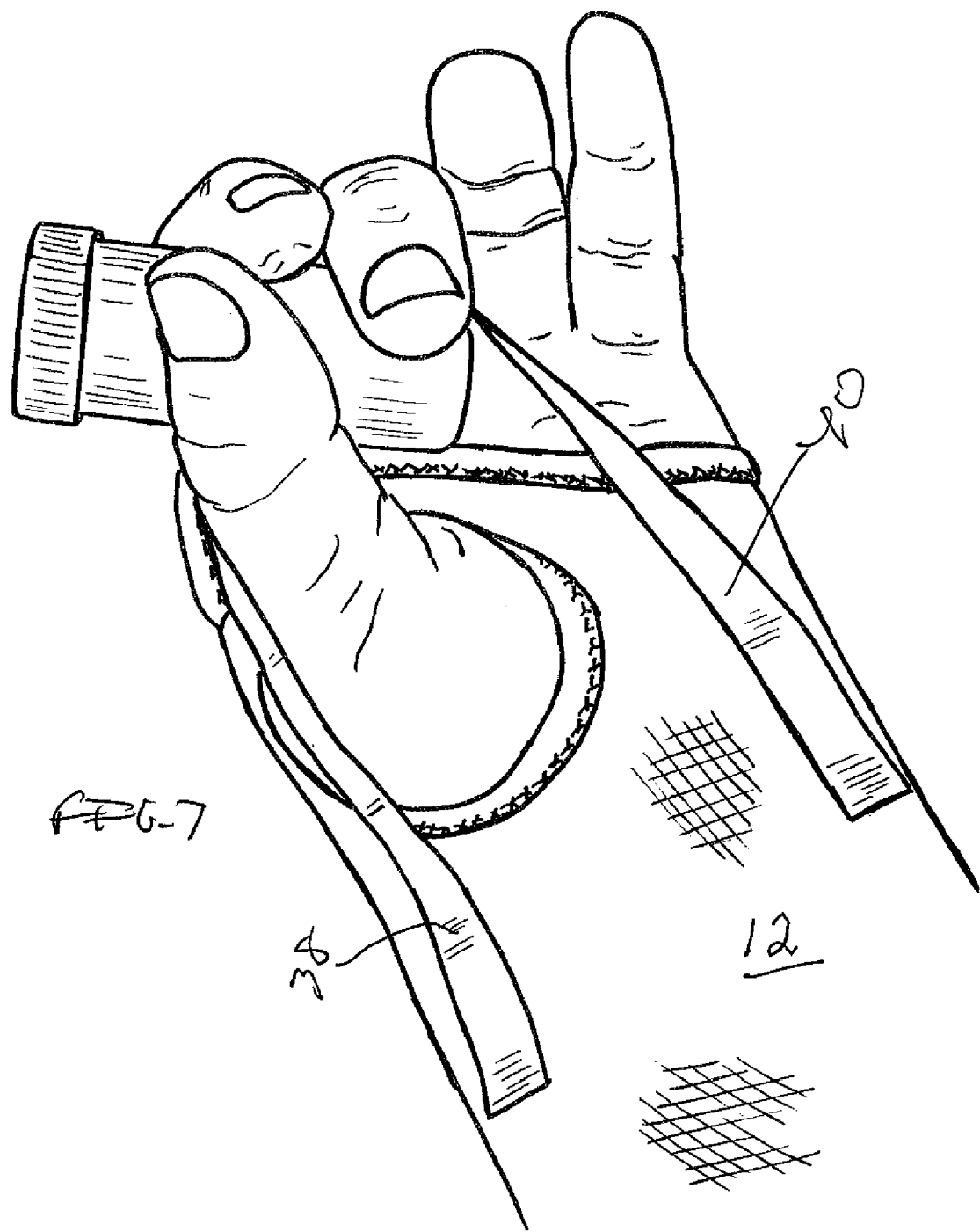
FIG. 7 is an isometric view similar to FIG. 6 but showing the finger-support sleeves of the finger-support section drawn and held tightly opposite the thumb via two "VELCRO" strips.
Figure 8:
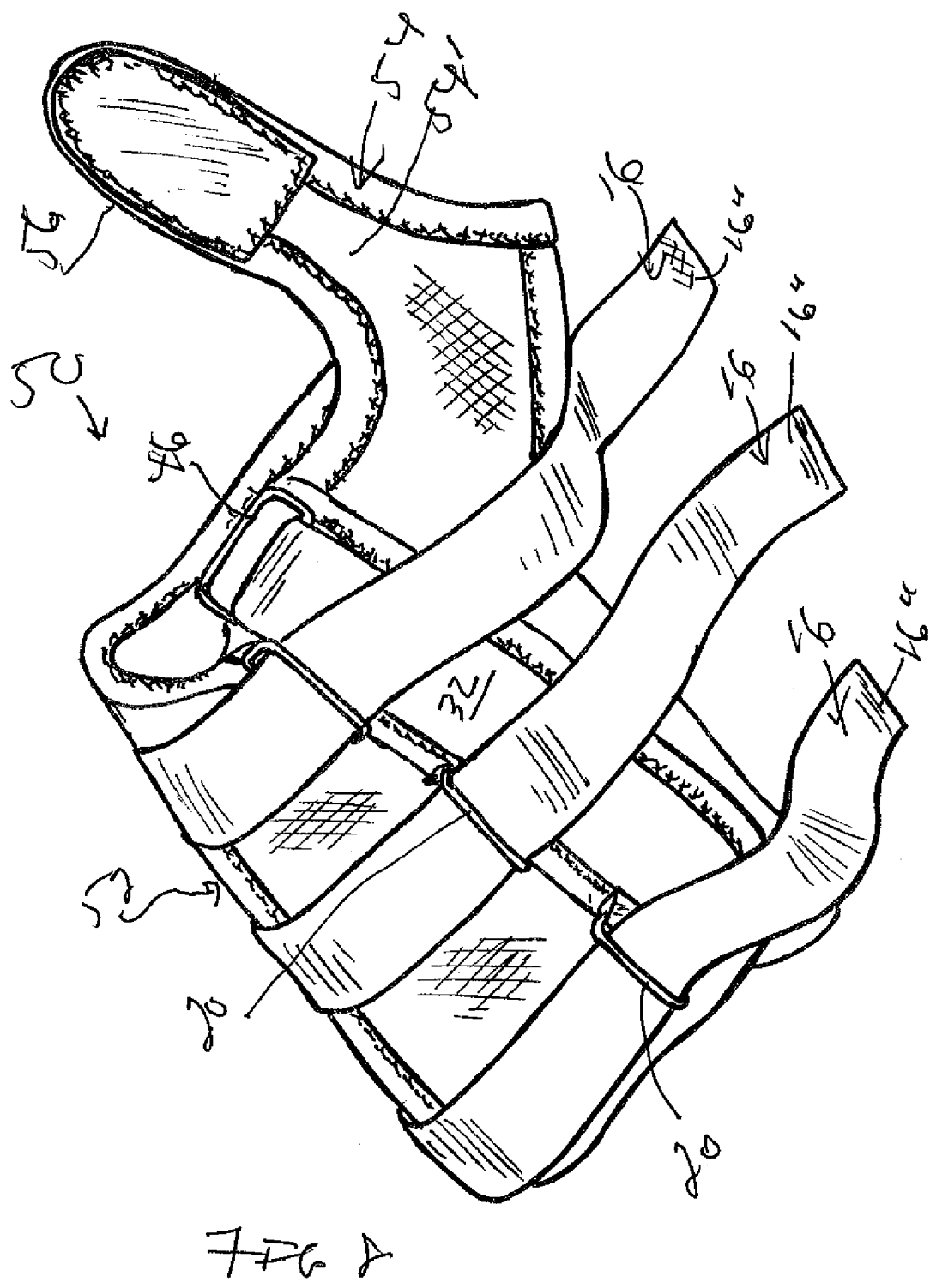
FIG. 8 is an isometric view of a second embodiment of the invention in which the wrist-sleeve support section of the digit-supporting therapeutic device for the fingers of a hand according to the invention is provided with an adjustably-fitting thumb sleeve.
Figure 9:
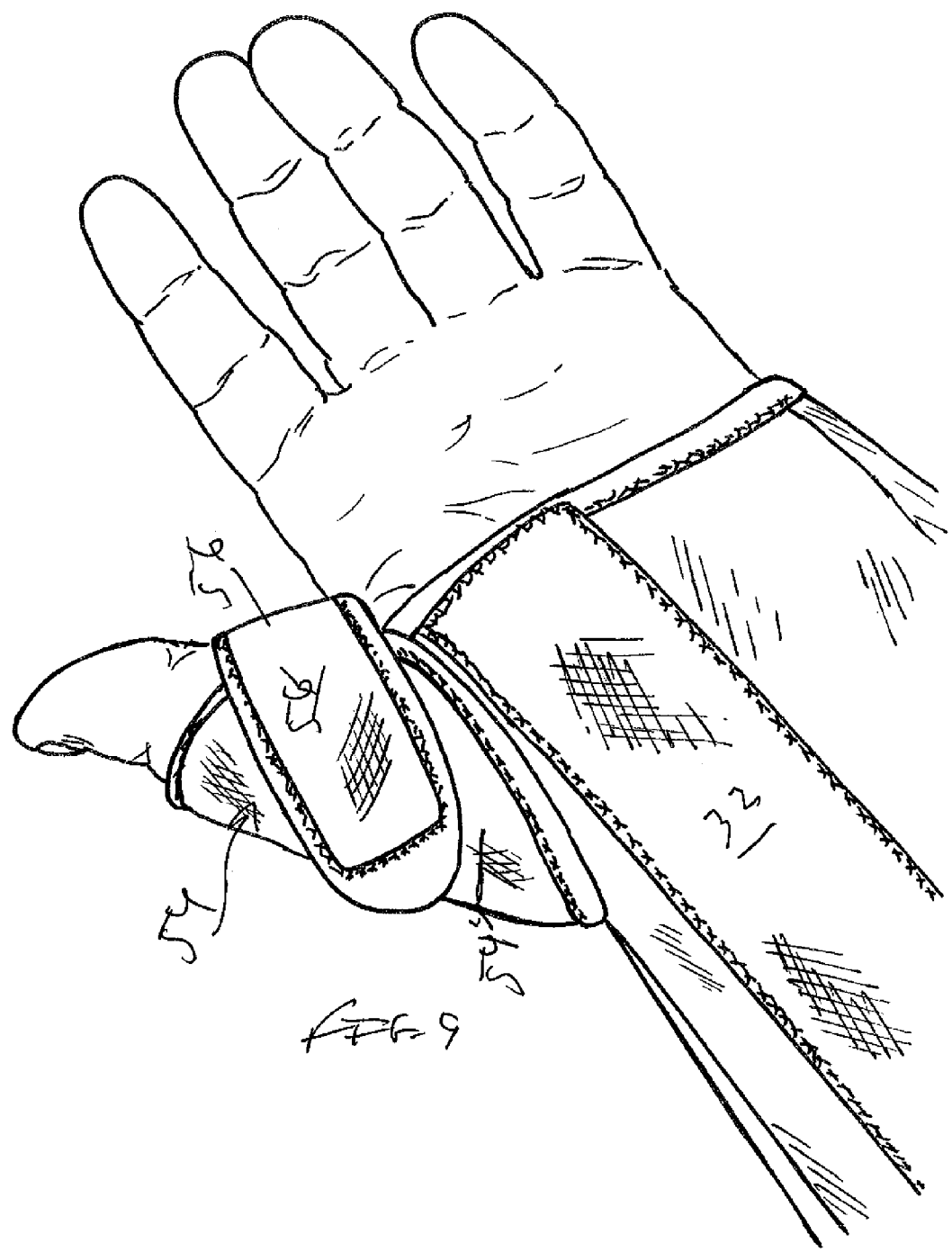
FIG. 9 is a front isometric view showing the wrist-sleeve support section of the second embodiment of FIG. 8 worn by the hand of user with the adjustably-fitting thumb-sleeve wrapped tightly about the thumb.
Figure 18:
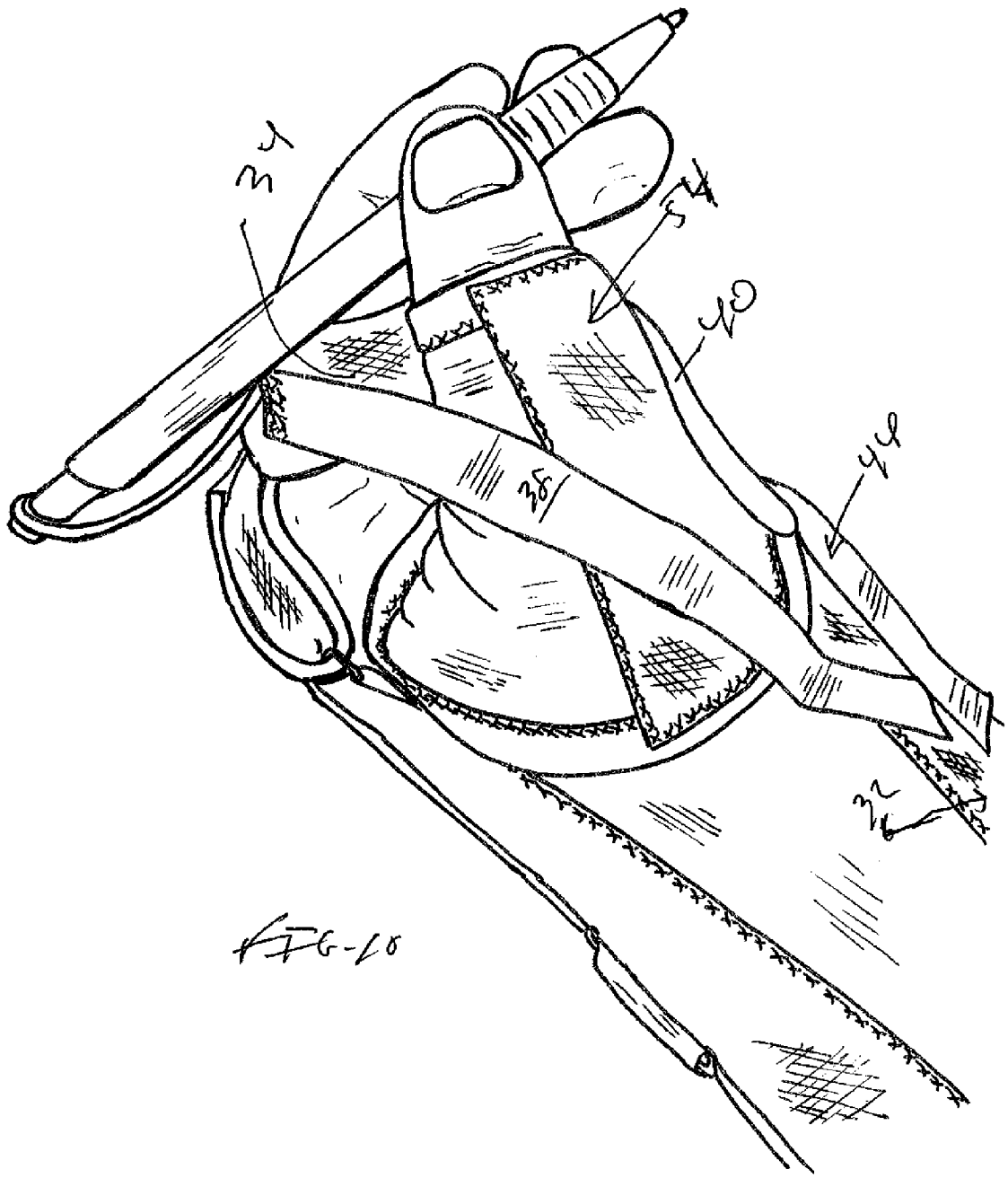

While the "VELCRO" strip 32 may be used for securing the adjustable mounting strips 38, 40 of the fingers-support section, it also possible to make much of the outer surface of the wrist-sleeve support section itself of the mating half-section portion of the hook-and-pile fastener, so that either of the strips 38, 40 may be alternatively secured to any surface portion of the wrist-sleeve support section having the mating hook-and-pile half-portions for the strips 38, 40. An example of this is shown in FIG. 7, where the strip 40 of the middle-finger sleeve is secured to a central surface area of the wrist-sleeve support section also provided with the mating half -portion of the hook-and-pile fastener of the straps 38, 40. By providing numerous "VELCRO" fastening surfaces for the fastening straps 38, 40, greater flexibility of securing and adjusting the fingers-support sleeve section to the wrist-sleeve support section is achieved.

Referring to FIG. 7, there is depicted how the therapeutic device 10 is used for holding, for example, a pill container. The straps 38 ,40 draw the fingers-support section 14 toward the protruding thumb. The straps 38, 40 are connected to chosen surface-areas of the wrist-support sleeve 12 to attain the desired biasing force of the fingers toward the thumb. The strap 38 may, if desired, be partially wrapped about the thumb provide additional support to the thumb. Also, while in FIG. 7 it has been shown that the pill box lies outside of the strap 38, if additional support is desired or required, the strap 38 may be partially wrapped about the pill box, or other object held, in order to provide even greater stability to the retained object. Owing to the large and multiple surface-areas of the wrist-support section 12 to which the straps 38, 40 may be attached, as described hereinabove, many variations of degree of support to the hand are provided, and may be changed by the user depending upon the object be held and particular need of the user, with the therapeutic device 10 of the invention affording numerous and different ways of the supporting an object between the index and middle fingers vis-a-vis the thumb, by means of the connection of the straps 38, 40 to many different "VELCRO" surfaces on the wrist-support sleeve.

Figure 11:
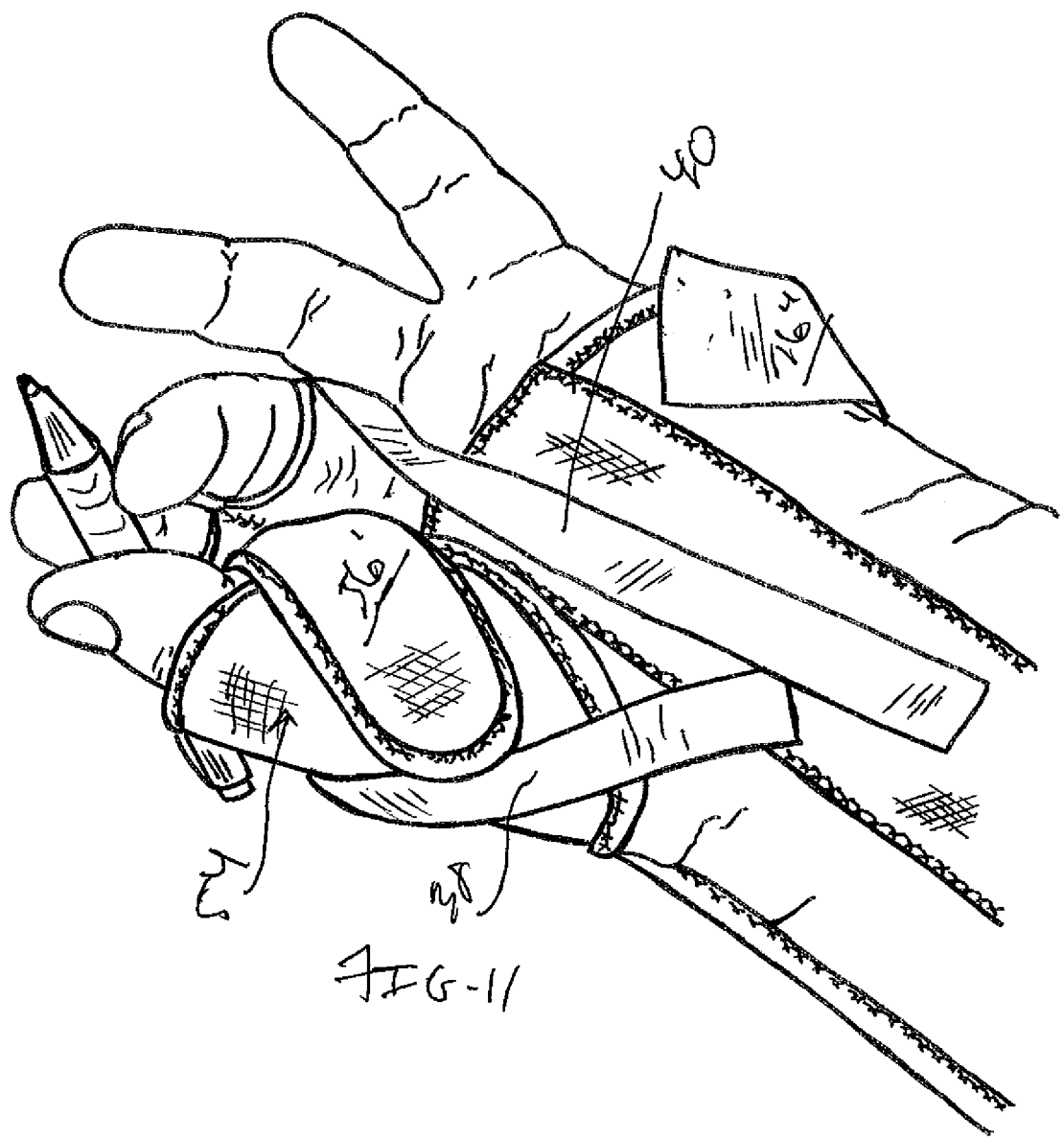
FIG. 11 is a front isometric view of FIG. 10.

Referring now to FIGS. 8-11, there is shown a second embodiment 50 of the invention. In this embodiment, the wrist-sleeve support section 52 is the same as that of the first embodiment with the exception of a thumb-sleeve 54, in the manner similar to that disclosed in Applicant's U.S. Pat. No. 6,887,212, while the fingers-support section is the same as the fingers-support section 14 of the first embodiment. The thumb-sleeve 54 consists of a first main portion 54' extending from and integral with the main body of the wrist-sleeve support section 54, and has a closure flap or section 56 that allows for accommodation of variously-sized thumbs. The closure strap and the first main portion 54' have cooperating hook-and-pile fastening elements for securing the thumb in place, in the manner depicted in FIG. 9. The other surface 56' of the flap 56, as well as the outer surface of the thumb-sleeve 54 proper, are also provided with "VELCRO" material for allowing the straps 38, 40 of the finger-support sleeves 34, 36 to be secured thereto, as shown in FIG. 10, in the manner described in Applicant's above-mentioned U.S. Pat. No. 6,887,212. As described hereinabove, most of the outer surface of the wrist-sleeve support section may be provided with "VELCRO" material so that the strap 40 of the finger-section 36 may be secured to a portion of the wrist-support sleeve other than the thumb sleeve 54, as shown in FIG. 11.

It is noted that other equivalent cooperating fasteners besides hook-and-pile may be used. Moreover, a version may be provided that includes a third finger-sleeve or with third and fourth finger-sleeves, in the manner disclosed in Applicant's above-mentioned U.S. Pat. No. 6,887,212. It is also noted, as disclosed in Applicant's above-mentioned U.S. Pat. No. 6,887,212, the fingers-support section is preferably, but not necessarily, be made of resilient, stretchable material. Also, the thumb-sleeve of the second embodiment may also, but not necessarily, be made of resilient, stretchable material. It is also noted that the two finger-sleeves may be for fingers of the hand other than the index and middle fingers.

It is also to be noted that the present invention contemplates that the separate fingers-support section may be used and attached to an existing or conventional hard or soft splint for the wrist, hand or fingers, as long as it has been adapted to allow for the connection of the connecting straps 38, 40, 44 thereto, and allow for the configuration of the two fingers in opposition to the thumb for a tripod pinch, and the like, as described above in detail. In this use, the wrist-support sleeve 12 of the invention is substituted for by the prior art splints and support devices.

Referring to FIGS. 10 and 11, there are depicted how the therapeutic device 50 is used for holding, for example, a pencil. The straps 38 ,40 draw the fingers-support section toward the protruding thumb from the thumb-sleeve. The straps 38, 40 are connected to the outer "VELCRO" surface of the thumb-sleeve 54, or to chosen surface-areas of the wrist-support sleeve 12 to attain the desired biasing force of the fingers toward the thumb. The straps 38, 40 may, if desired, be wrapped about the thumb-sleeve 54 in order to provide additional support to the thumb. Also, while in FIGS. 10 and 11, it has been shown that the pencil lies outside of the straps 38, 40, if additional support is desired or required, the strap 38 or strap 40 may be partially wrapped about the pencil, or other object held, in order to provide even greater stability to the retained object. Owing to the large and multiple surface-areas of the wrist-support section to which the straps 38, 40 may be attached, as described hereinabove, many variations of degree of support to the hand are provided, and may be changed by the user depending upon the object to be held and particular need of the user, and may be changed by the user depending upon the object to be held and particular need of the user, with the therapeutic device 50 of the invention affording numerous and different ways of the supporting an object between the index and middle fingers vis-à-vis the thumb, by means of the connection of the straps 38, 40 to many different "VELCRO" surfaces on the wrist-support sleeve.

While specific embodiments of the invention have been shown and described, it is to be understood that numerous changes and modifications may be made therein without departing from the scope and spirit of the invention as set forth in the appended claims.

The invention claimed is:

1. A method of using a therapeutic device for the fingers of a hand, which therapeutic device comprises finger-support sleeve means for insertion therein of at least two fingers of a hand, and strap means for placing the finger-support sleeve means in opposition to the thumb of a hand, the finger-support sleeve means in combination with the thumb forming a space therebetween for holding an object, said method comprising:
    (a) attaching the finger-support sleeve means to at least two fingers of a hand;
    (b) placing the finger-support sleeve means with inserted fingers therein in opposition to the thumb of the hand via the strap means for placing the finger-support sleeve means in opposition to the thumb of a hand;
    (c) said step (b) forming a tripod pinch between the finger-support sleeve means and the thumb of the hand;
    (d) inserting an object in the space between the finger-support sleeve means and the thumb of the hand;
    (e) said step (b) comprising maintaining the thumb and the finger-support sleeve means in opposing position by the strap means for placing the finger-support sleeve means in opposition to the thumb of a hand in order to maintain the tripod pinch of said step (c), whereby the thumb and at least some of the other fingers of the hand are supported for holding the object of said step (d).

2. The method of using a therapeutic device for the fingers of a hand according to claim 1, wherein said step (b) comprises removably and adjustably securing the finger-support sleeve means to a wrist-support section from which a thumb projects; said step (e) comprising adjusting and tightening the strap means.

* * * * *